United States Patent [19]

Araki et al.

[11] Patent Number: 5,750,816

[45] Date of Patent: May 12, 1998

[54] PROCESS FOR THE PREPARATION OF α-OLEFIN OLIGOMERS

[75] Inventors: Yoshitaka Araki; Takashi Ishikawa; Hirofumi Nakamura; Akio Tsuboi; Yoshiaki Nanba; Takeshi Okano, all of Kurashiki; Takayuki Aoshima, Yokohama; Shinji Iwade, Kurashiki, all of Japan

[73] Assignee: Mitsubishi Chemical Corporation, Japan

[21] Appl. No.: 609,431

[22] Filed: Mar. 1, 1996

[30] Foreign Application Priority Data

| Mar. 2, 1995 | [JP] | Japan | 7-068603 |
| Mar. 2, 1995 | [JP] | Japan | 7-068604 |
| Apr. 18, 1995 | [JP] | Japan | 7-092603 |
| Dec. 21, 1995 | [JP] | Japan | 7-349702 |
| Dec. 26, 1995 | [JP] | Japan | 7-351578 |

[51] Int. Cl.$^6$ .................................................. C07C 2/30
[52] U.S. Cl. ........................ 585/512; 585/513; 585/520; 585/527
[58] Field of Search .......................... 585/512, 513, 585/520, 527

[56] References Cited

U.S. PATENT DOCUMENTS

| 3,347,840 | 10/1967 | Manyik et al. . | |
| 4,668,838 | 5/1987 | Briggs . | |
| 4,777,315 | 10/1988 | Levine et al. | 585/513 |
| 4,853,356 | 8/1989 | Briggs . | |
| 5,198,563 | 3/1993 | Reagen et al. . | |
| 5,288,823 | 2/1994 | Reagan et al. . | |
| 5,331,104 | 7/1994 | Reagen et al. . | |
| 5,376,612 | 12/1994 | Reagen et al. . | |
| 5,382,738 | 1/1995 | Reagen et al. | 585/512 |
| 5,438,027 | 8/1995 | Reagen et al. | 585/512 |
| 5,491,272 | 2/1996 | Tanaka et al. . | |

FOREIGN PATENT DOCUMENTS

| 0 237 079 | 9/1987 | European Pat. Off. . |
| 0 416 304 A2 | 3/1991 | European Pat. Off. . |
| 0417477 | 3/1991 | European Pat. Off. . |
| 0 537 609 A2 | 4/1993 | European Pat. Off. . |
| 0537609 | 4/1993 | European Pat. Off. . |
| 0 608 447 A1 | 8/1994 | European Pat. Off. . |
| 0 611 743 A2 | 8/1994 | European Pat. Off. . |
| 0 611 743 A3 | 8/1994 | European Pat. Off. . |
| 0611743 | 8/1994 | European Pat. Off. . |
| 0 614 865 A1 | 9/1994 | European Pat. Off. . |
| 0614865 | 9/1994 | European Pat. Off. . |
| 0 622 347 A1 | 11/1994 | European Pat. Off. . |
| 06329562 A | 11/1994 | Japan . |
| 6-329562 | 11/1994 | Japan . |
| 07017878 A | 1/1995 | Japan . |
| 7-10780 | 1/1995 | Japan . |
| WO 94/15940 | 7/1994 | WIPO . |

OTHER PUBLICATIONS

Seidel et al: "Über die Darstellung neuer Phenylchrom–Komplexe," *Zeitschrift für anorganische und allgemeine Chemie*, Band 404, Mar. 1974, pp. 225–229.

Reagen: Chromium (II) and (III) pyrrolyl Ethylene Oligomerization Catalysts, Synthesis and Crystal Structure of Square Planar $Cr(NC_4H_4)_4$–2, and Pentanuclear $Cr_5(NC_4H_4)_{10}(OC_4H_8)_1$ Symposium on Novel Preparation and Conversion of Light Olefins Presented Before the Division of Petroleum Chemistry, Inc., American Chemical Society, 1989, pp. 583–588 month unavailable.

Davies et al: "Chromium(III) Chelates of Some 2–Acylpyrroles", *J. inorg. nucl.*, Chem. 1972, vol. 34, pp. 2791–2795 date unavailable.

Edema et al: "The Unpredictable Structural Features of Chromium(II) Pyrrolyls: Synthesis and X-ray Structures of Monomeric Square–Planar $(\eta^1-2,5-Me_2D_4H_2N)_2Cr(py)_{2l}$, Square–Pyramidal $(\eta^1-C_4H_4N)_2CR(py)_3$, Dimeric $[(7–azaindolyl)_2Dr(DMF)]_2$, and Polymeric $[(\eta^1-2,5-Me_2C_4N_2)_4CrNa_2(THF)_2(Et_2O)]_n$. An Aborted Cr—Cr Quadruple Bond Formation?," *Inorg. Chem.* 1990, 29, pp. 2147–2153 month unavailable.

*Primary Examiner*—Jacqueline V. Howard
*Attorney, Agent, or Firm*—Nixon & Vanderhye

[57] ABSTRACT

An oligomerization of α-olefins is carried out in a solvent using a chromium-based catalyst system comprising at least (a) a chromium compound, (b) at least one nitrogen-containing compound selected from amines, amides and imides, and (c) an alkylaluminum compound, and the catalyst components and by-product polymers are recovered simultaneously from the reaction solution. Such process is an industrially advantageous process for producing α-olefin oligomers by using a chromium-based catalyst, and is simple and capable of efficiently recovering the by-product polymers and the catalyst components simultaneously.

29 Claims, No Drawings

PROCESS FOR THE PREPARATION OF α-OLEFIN OLIGOMERS

BACKGROUND OF THE INVENTION

The present invention relates to a process for preparing α-olefin oligomers. More particularly, it relates to an industrially advantageous process for preparing α-olefin oligomers, according to which it is possible to prepare α-olefin oligomers comprising 1-hexene as main component from ethylene in a high yield with high selectivity.

As an oligomerization method of α-olefin such as ethylene, methods using a chromium-based catalyst comprising a combination of a specific chromium compound and a specific organic aluminum compound have been known. For instance, Japanese patent Publication (KOKOKU) No. 43-18707 discloses a process for producing 1-hexene from ethylene by using a catalytic system consisting of a chromium-containing Group VIA transition metal compound and polyhydrocarbylaluminum oxide.

Also, Japanese Patent Application Laid-Open (KOKAI) No. 3-128904 discloses a method for trimerizing α-olefins by using a catalyst obtained by reacting a chromium-containing compound having chrome-pyrrolyl bond with an alkyl metal or a Lewis acid.

In either of the said methods, formation of by-product polymers is unavoidable, and it is now a great technical problem in the art how to separate the by-product polymers in the industrial production of α-olefin oligomers. High-purity preparation of α-olefin oligomers is also of importance for application of the obtained oligomers. Further, removal of the catalyst components such as chromium compound contained in the reaction solution is an important subject since such catalyst components may deposit on the distillation column depending on the distillation conditions to give rise to various problems.

As a result of the present inventors' earnest studies, it has been found that by carrying out an oligomerization reaction of α-olefins in a solvent in the presence of a chromium-based catalyst system comprising at least (a) a chromium compound, (b) at least one nitrogen-containing compound selected from the group consisting of amines, amides and imides, and (c) an alkylaluminum compound, and separating the produced α-olefin oligomers, catalyst components and by-product polymers from the reaction solution, wherein the catalyst components and the by-product polymers are separated simultaneously from the reaction solution, the produced by-product polymers and catalyst components can be efficiently separated, and the process can be simplified and is industrially advantageous. On the basis of the finding, the present invention has been attained.

SUMMARY OF THE INVENTION

An object of the present invention is to provide an industrially advantageous process for preparing α-olefin oligomers by using a chromium-based catalyst, which process is simple and capable of efficiently separating the by-product polymers and catalyst components.

In a first aspect of the present invention, there is provided a process for producing α-olefin oligomers, which comprises carrying out an oligomerization reaction of α-olefins in a solvent in the presence of a chromium-based catalyst system comprising at least (a) a chromium compound, (b) at least one nitrogen-containing compound selected from the group consisting of amines, amides and imides, and (c) an alkylaluminum compound, and recovering the produced α-olefin oligomers, catalyst components and by-product polymers from the reaction solution, wherein the catalyst components and the by-product polymers are recovered simultaneously from the reaction solution.

In a second aspect of the present invention, there is provided a process for producing α-olefin oligomers, which comprises carrying out an oligomerization of α-olefins in the presence of a reaction solvent in an oligomerization reactor by using a chromium-based catalyst system comprising at least (a) a chromium compound, (b) at least one nitrogen-containing compound selected from the group consisting of amines, amides and imides, and (c) an alkylaluminum compound, supplying the resulting reaction solution into a degassing tower to recover the unreacted α-olefins, supplying the reaction solution from the degassing tower into a product distillation tower to recover the produced α-olefin oligomers as a distillate while concentrating the by-product polymers and catalyst components, and recovering the concentrated by-product polymers and catalyst components as bottoms, wherein the by-product polymers and catalyst components are maintained in a dispersed state in the reaction solution in the process line from the outlet of the oligomerization reactor to the inlet of the product distillation tower.

DETAILED DESCRIPTION OF THE INVENTION

The present invention is described in detail below.

In the present invention, a chromium-based catalyst system comprising at least (a) a chromium compound, (b) at least one nitrogen-containing compound selected from the group consisting of amines, amides and imides, and (c) an alkylaluminum compound, is used as catalyst for the oligomerization reaction. In the preferred embodiments of the present invention, there is used a catalyst system comprising a combination of (a) a chromium compound, (b) at least one nitrogen-containing compound selected from the group consisting of amines, amides and imides, (c) an alkylaluminum compound, and (d) a halogen-containing compound.

The chromium compound (a) usable in the present invention is represented by the formula: $CrX_n$, wherein X is an organic group, an inorganic group or an anionic atom; n is an integer from 1 to 6, and when n is not less than 2, X's may be identical or different from each other. The valency of chromium is 0 to 6, and n in the above formula is preferably not less than 2.

The organic groups represented by X in the above formula include various kinds of groups having a carbon number of usually 1 to 30, such as hydrocarbon group, carbonyl group, alkoxyl group, carboxyl group, β-diketonate group, β-ketocarboxyl group, β-ketoester group and amide group. The hydrocarbon group includes alkyl group, cycloalkyl group, aryl group, alkylaryl group, aralkyl group, cyclopentadienyl group, etc. The inorganic groups represented by X include the chromium salt-forming groups such as nitric group and sulfuric group. The anionic atoms include oxygen atom, halogen atom, etc.

Preferred examples of the chromium compounds usable in the present invention are chromium alkoxides, chromium carboxylates, chromium β-diketonates and salts of chromium with anions of β-ketoester, and chromium halides. More specifically, chromium (IV)-t-butoxide, chromium (III) acetylacetonate, chromium (III) trifluoroacetylacetonate, chromium (III) hexafluoroacetylacetonate, chromium (III) (2,2,6,6- tetramethyl-3,5-heptanedionate), Cr(PhCOCHCOPh)$_3$ (wherein Ph represents phenyl group), chromium (II) acetate, chromium (III) acetate, chromium (III) 2-ethylhexanoate, chromium (III) benzoate, chromium (III) naphthenate, Cr(CH$_3$COCHCOOCH$_3$)$_3$, chromous chloride, chromic chloride, chromous bromide, chromic bromide, chromous iodide, chromic iodide, chromous fluoride and chromic fluoride may be exemplified.

Complexes composed of the said chromium compounds and electron donors can also favorably be used. The electron donors are selected from the nitrogen-containing compound, oxygen-containing compound, phosphorus-containing compound or sulfur-containing compound.

The nitrogen-containing compound used as a constituent of the catalyst system in the present invention is selected from nitriles, amines, amides, etc., such as acetonitrile, pyridine, dimethylpyridine, dimethylformamide, N-methylformamide, aniline, nitrobenzene, tetramethylethylenediamine, diethylamine, isopropylamine, hexamethyldisilazane and pyrrolidone.

The oxygen-containing compounds usable as another constituent of the said catalyst system include esters, ethers, ketones, alcohols, aldehydes, etc., such as ethyl acetate, methyl acetate, tetrahydrofuran, dioxane, diethyl ether, dimethoxyethane, diethylene glycol dimethyl ether, triethylene glycol dimethyl ether, acetone, methyl ethyl ketone, methanol, ethanol, and acetaldehyde.

The phosphorus-containing compounds include hexamethylphosphoramide, hexamethylphosphorustriamide, triethyl phosphite, tributylphosphine oxide, triethylphosphine, etc.

The sulfur-containing compounds include carbon disulfide, dimethyl sulfoxide, tetramethylene sulfone, thiophene, dimethyl sulfide, etc.

Then, the complexes composed of chromium compounds and electron donors usable in the present invention include ether complexes, ester complexes, ketone complexes, aldehyde complexes, alcohol complexes, amine complexes, nitrile complexes, phosphine complexes and thioether complexes of chromium halides, specifically CrCl$_3$.3THF, CrCl$_3$.3dioxane, CrCl$_3$.(CH$_3$CO$_2$-n-C$_4$H$_9$), CrCl$_3$.(CH$_3$CO$_2$C$_2$H$_5$), CrCl$_3$.3(i-C$_3$H$_7$OH), CrCl$_3$.3[CH$_3$(CH$_2$)$_3$CH(C$_2$H$_5$)CH$_2$OH], CrCl$_3$.3pyridine, CrCl$_3$.2(i-C$_3$H$_7$NH$_2$), [CrCl$_3$.3CH$_3$CN].CH$_3$CN, CrCl$_3$.3PPh$_3$, CrCl$_2$.2THF, CrCl$_2$.2pyridine, CrCl$_2$.2[(C$_2$H$_5$)$_2$NH], CrCl$_2$.2CH$_3$CN, CrCl$_2$.2[P(CH$_3$)$_2$Ph], etc.

The chromium compound used in the present invention is preferably one which is soluble in hydrocarbon solvents. Examples of such chromium compound include chromium β-diketonate, chromium carboxylates, salts of chromium with anions of β-ketoester, chromium β-ketocarboxylates, chromium amide complexes, chromium carbonyl complexes, chromium carbene complexes, various types of cyclopentadienyl complexes of chromium, chromium alkyl complexes, chromium phenyl complexes, etc. As specific examples thereof, Cr(CO)$_6$, (C$_6$H$_6$)Cr(CO)$_3$, (CO)$_5$Cr (=CCH$_3$ (OCH$_3$)), (CO)$_5$Cr (=CC$_6$H$_5$ (OCH$_3$)), CpCrCl$_2$ (wherein Cp represents cyclopentadienyl group), (Cp*CrClCH$_3$)$_2$ (wherein Cp* represents pentamethylcyclopentadienyl group), and (CH$_3$)$_2$CrCl may be exemplified.

The chromium compound may be supported on a carrier such as an inorganic oxide, but it is preferably used in combination with other catalyst components without being supported on a carrier. In the present invention, the chromium-based catalyst is preferably used in a specific contacting mode described later because when the catalyst is used in such a mode, a high catalyst activity can be obtained even if the chromium compound is not supported on a carrier. Further, when the chromium compound is used without being supported on a carrier, it is possible to dispense with the complicated operation necessary for supporting the compound on a carrier, and moreover, the problem of increase of the total amount of the catalyst used (sum of the carrier and the catalyst components) can be evaded.

The amine used in the present invention is selected from primary amines and secondary amines. The primary amines include ethylamine, isopropylamine, cyclohexylamine, benzylamine, aniline, naphthylamine, etc. The secondary amines include diethylamine, diisopropylamine, dicyclohexylamine, dibenzylamine, bis(trimethylsilyl) amine, morphorine, imidazole, indoline, indole, pyrrole, 2,5-dimethylpyrrole, 3,4-dimethylpyrrole, 3,4-dichloropyrrole, 2,3,4,5-tetrachloropyrrole, 2-acetylpyrrole, pyrazole, pyrrolidine, dipyrrolomethane, etc.

The amides usable in the present invention include metal amides derived from primary or secondary amines, for example, amides obtained from reaction of primary or secondary amines such as mentioned above with metals selected from IA, IIA, IIIB and IVB Groups of the periodic table. Examples of such metal amides are lithium amide, sodium ethylamide, calcium diethylamide, lithium diisopropylamide, potassium benzylamide, sodium bis (trimethylsilyl)amide, lithium indolide, sodium pyrrolide, lithium pyrrolide, potassium pyrrolide, potassium pyrrolidide, diethylaluminum pyrrolide, ethylaluminum dipyrrolide, aluminum tripyrrolide, sodium 2,5-dimethylpyrrolide, lithium 2,5-dimethylpyrrolide, potassium 2,5-dimethylpyrrolide, potassium 2,5-dimethylpyrrolidide, diethylaluminum 2,5-dimethylpyrrolide, ethylaluminum di(2,5-dimethylpyrrolide), and aluminum tri(2,5-dimethylpyrrolide).

In the present invention, the secondary amines such as mentioned above, the metal amides derived from such secondary amines, and mixtures thereof are preferably used. Preferred examples of such secondary amines are pyrrole and pyrrole derivatives such as 2,5-dimethylpyrrole, 3,4-dimethylpyrrole, 3,4-dichloropyrrole, 2,3,4,5-tetrachloropyrrole, 2-acetylpyrrole and dipyrrolomethane and preferred examples of metal amides derived from the said secondary amines are aluminum pyrrolide, ethylaluminum dipyrrolide, aluminum tripyrrolide, sodium pyrrolide, lithium pyrrolide, potassium pyrrolide, aluminum 2,5-dimethylpyrrolide, ethylaluminum di(2,5-dimethylpyrrolide), aluminum tri(2,5-dimethylpyrrolide), sodium 2,5-dimethylpyrrolide, lithium 2,5-dimethylpyrrolide, and potassium 2,5-dimethylpyrrolide. Of these pyrroles, those having a hydrocarbon group in the pyrrole ring are preferred.

Other amide and imide compounds usable in the present invention include those represented by the following formulae (1)–(3):

 (1)

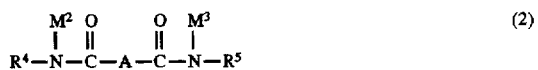 (2)

In the formula (1) M$^1$ is hydrogen atom or a metal element selected from IA, IIA and IIB Groups of the periodic table; R$^1$ is hydrogen atom, C$_1$–C$_{30}$ alkyl group, C$_1$–C$_{30}$ alkenyl group, $C_1$–$C_{30}$ aralkyl group, aryl group which may have a substituent, or aryl group which may contain a hetero element; $R^2$ is hydrogen atom, $C_1$–$C_{30}$ alkyl group, $C_1$–$C_{30}$ alkenyl group, $C_1$–$C_{30}$ aralkyl group, aryl group which may have a substituent, aryl group which may contain a hetero element, or acryl group: —C(=O)$R^3$ (wherein $R^3$ may be identical with $R^1$ or different from $R^1$); $R^1$ and $R^2$ may form a ring.

In the formula (2) $M^2$ and $M^3$ are each hydrogen atom or a metal element selected from IA, IIA and IIIB Groups of the periodic table; $R^4$ and $R^5$ are each hydrogen atom or $C_1$–$C_{30}$ alkyl group, $C_1$–$C_{30}$ alkenyl group, $C_1$–$C_{30}$ aralkyl group, aryl group which may have a substituent, or aryl group which may contain a hetero element; $R^4$ and $R^5$ may form a ring; and A is alkylene group which may contain an unsaturated bond.

In the formula (3) $M^4$ is hydrogen atom or a metal element selected from IA, IIA and IIIB Groups of the periodic table; $R^6$ is hydrogen atom, $C_1$–$C_{30}$ alkyl group, $C_1$–$C_{30}$ alkenyl group, $C_1$–$C_{30}$ aralkyl group, aryl group which may have a substituent, or aryl group which may contain a hetero element; $R^7$ is hydrogen atom, $C_1$–$C_{30}$ alkyl group, $C_1$–$C_{30}$ alkenyl group, $C_1$–$C_{30}$ aralkyl group, aryl group which may have a substituent, aryl group which may contain a hetero element, or $SO_2R^8$ (wherein $R^8$ may be identical with $R^6$ or different from $R^6$); $R^6$ and $R^7$ may form a ring.

The amides represented by the formula (1) or (2) include acetamide, N-methylhexaneamide, succineamide, maleamide, N-methylbenzamide, imidazole-2-carboxamide, di-2-thenoylamine, β-lactam, δ-lactam, ε-lactam, and salts thereof with metals of IA, IIA or IIIB Group of the periodic table. The imides represented by the formula (1) or (2) include 1,2-cyclohexanedicarboxyimide, succineimide, phthalimide, maleimide, 2,4,6-piperidinetrione, perhydroazesine-2,10-dione, and salts thereof with metals of IA, IIA or IIIB Group of the periodic table.

The sulfoneamides and sulfoneimides represented by the formula (3) include benzene sulfoneamide, N-methylmethane sulfoneamide, N-methyltrifluoromethane sulfoneamide, and salts thereof with metals of IA, IIA or IIIB Group of the periodic table.

Of these amide and imide compounds, those represented by the formula (1) are preferred, and the imide compounds of the formula (1) wherein $R^2$ represents acyl group: —C(=O)$R^3$, and $R^1$ and $R^2$ form a ring, are particularly preferred.

The alkylaluminum compound (c) used as a constituent of the catalyst system in the present invention is preferably selected from those represented by the following formula (4):

$$R^1_m Al(OR^2)_n H_p X_q \quad (4)$$

wherein $R^1$ and $R^2$ may be identical or different and each represents usually $C_1$–$C_{15}$ hydrocarbon group, preferably $C_1$–$C_8$ hydrocarbon group; X is halogen atom; m, n, p and q are numbers defined by 0<m≦3, 0<n≦3, 0≦p<3, 0≦q<3, and m+n+p+q=3.

The alkylaluminum compounds defined above include trialkylaluminum compounds represented by the following formula (5), alkylaluminum halides represented by the following formula (6), alkoxyalkylaluminum compounds represented by the following formula (7), and alkylaluminum hydrides represented by the following formula (8). In these formulae, $R^1$, X and $R^2$ are as defined in the formula (4).

$$R^1_3 Al \quad (5)$$

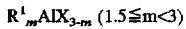

$$R^1_m AlX_{3-m} \quad (1.5 \leq m < 3) \quad (6)$$

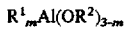

$$R^1_m Al(OR^2)_{3-m}$$

(0<m<3, preferably 1.5≦m<3)     (7)

$$R^1_m AlH_{3-m}$$

(0<m<3, preferably 1.5≦m<3)     (8)

Examples of the above-defined alkylaluminum compounds include trimethylaluminum, triethylaluminum, triisobutylaluminum, diethylaluminum monochloride, diethylaluminum ethoxide, diethylaluminum hydride, etc. Of these, trialkylaluminum is preferred because of minimized formation of by-product polymers. These alkylaluminum compounds may be used as a mixture of two or more of them.

The halogen-containing compound (d) used as another constituent of the catalyst system in the present invention is preferably selected from those containing an element of IIIA, IIIB, IVA, IVB, VA or VB Group of the periodic table. The halogen contained in the compound is preferably chlorine or bromine.

Examples of such halogen-containing compounds are scandium chloride, yttrium chloride, lanthanum chloride, titanium tetrachloride, zirconium tetrachloride, hafnium tetrachloride, boron trichloride, aluminum chloride, diethylaluminum chloride, ethylaluminum dichloride, ethylaluminum sesquichloride, gallium chloride, carbon tetrachloride, chloroform, methylene chloride, dichloroethane, trichloroethane, tetrachloroethane, hexachlorobenzene, hexachloroethane, 1,3,5-trichlorobenzene, hexachlorocyclohexane, trityl chloride, silane tetrachloride, trimethylchlorosilane, germanium tetrachloride, tin tetrachloride, tributyltin chloride, phosphorus trichloride, antimony trichloride, trityl hexachloroantimonate, antimony pentachloride, bismuth trichloride, boron tribromide, aluminum tribromide, carbon tetrabromide, bromoform, bromobenzene, iodomethane, silicon tetrabromide, hexafluorobenzene, aluminum fluoride, allyl chloride, 1,1-dichloroacetone, 1,1,1-trichloroacetone, 1,1,3-trichloroacetone, etc.

Of these halogen-containing compounds, those having a large number of halogen atoms or those soluble in the reaction solvent are preferably used. Particularly preferred examples are carbon tetrachloride, chloroform, hexachloroethane, tetrachloroethane, titanium tetrachloride, germanium tetrachloride, tin tetrachloride, diethylaluminum chloride, ethylaluminum dichloride, ethylaluminum sesquichloride and the like. These halogen-containing compounds may be used in admixture.

In the present invention, an α-olefin is subjected to an oligomerization reaction using a chromium-based catalyst such as mentioned above in a reaction solvent in an oligomerization reactor. Usually a tubular reactor, or a single- or multiple-stage mixing tank is used as the polymerization reactor. The tubular reactor is basically a reactor in which the reactants are introduced from an end of a straight tube, or a coiled or U-shaped bent pipe and the reaction product is discharged from the other end. Multiple-stage mixing tank is basically a reactor in which the reactants are introduced into the first of a plurality of mixing tanks arranged in series and successively passed into the succeeding tanks, and the reaction product is discharged from the final tank.

In the present invention, the oligomerization reaction is carried out in such a contacting mode that before an α-olefin and a chromium-based catalyst are contacted with each other, that is before the oligomerization reaction is started with the catalyst components (a)–(c) and optionally (d) and the α-olefin being allowed to exist together, the chromium compound (a) and the alkylaluminum compound (c) do not come previously into contact with each other. By employing such a specific contacting mode, it is possible to carry out the desired trimerization reaction with high activity and high selectivity to obtain 1-hexene from the starting ethylene in a high yield.

As to the said specific contacting mode, the following various ways may be exemplified.

(1) Method of introducing the chromium compound (a) and the α-olefin into a solution containing the nitrogen-containing compound (b), the alkylaluminum compound (c) and optionally, the halogen-containing compound (d).

(2) Method of introducing the alkylaluminum compound (c) and the α-olefin into a solution containing the chromium compound (a), the nitrogen-containing compound (b) and optionally, the halogen-containing compound (d).

(3) Method of introducing the nitrogen-containing compound (b), the alkylaluminum compound (c) and the α-olefin into a solution containing the chromium compound (a) and optionally, the halogen-containing compound (d).

(4) Method of introducing the chromium compound (a), the nitrogen-containing compound (b) and the α-olefin into a solution containing the alkylaluminum compound (c) and optionally, the halogen-containing compound (d).

(5) Method of introducing the α-olefin, the alkylaluminum compound (c) and optionally, the halogen-containing compound (d) into a solution containing the chromium compound (a) and the nitrogen-containing compound (b).

(6) Method of introducing the α-olefin, the chromium compound (a) and optionally, the halogen-containing compound (d) into a solution containing the nitrogen-containing compound (b) and the alkylaluminum compound (c).

(7) Method of introducing the α-olefin, the chromium compound (a), the nitrogen-containing compound (b) and optionally, the halogen-containing compound (d) into a solution containing the alkylaluminum compound (c).

(8) Method of introducing the α-olefin, the nitrogen-containing compound (b), the alkylaluminum compound (c) and optionally, the halogen-containing compound (d) into a solution containing the chromium compound (a).

(9) Method of introducing the α-olefin, the chromium compound (a), the nitrogen-containing compound (b), the alkylaluminum compound (c) and optionally, the halogen-containing compound (d) into a reaction system simultaneously and independently of each other.

In each case, the said solution is usually prepared using a reaction solvent.

In the present invention, the expression "such a contacting mode that the chromium compound and the alkylaluminum compound do not come previously into contact with each other" means that such a contacting mode is maintained not only before the initiation of the oligomerization reaction but also during additional supply of α-olefin and catalyst components into the reactor. But this specific contacting mode is a mode required in catalyst preparation and is of no significance after preparation of the catalyst. Therefore, the catalyst recovered from the reaction system can be recycled to the reaction system without contradicting the said specific contacting mode.

The reason why the α-olefin oligomerization reaction activity is reduced when using a chromium-based catalyst in such a manner that the chromium compound and the alkylaluminium compound are previously contacted with each other is yet to be accounted for, but the following is estimated.

It is considered that when a chromium compound and an alkylaluminum compound are contacted with each other, there takes place a ligand exchange reaction between the ligand coordinating in the chromium compound and the alkyl group in the alkylaluminum compound. The alkyl-chromium compound produced by this reaction is per se unstable unlike the alkyl-chromium compound obtained by the ordinary method. Therefore, a decomposition/reduction reaction of the alkyl-chromium compound advances preferentially, thereby causing demetallization unfavorable for the oligomerization reaction of α-olefins, and this presumably leads to a reduction of the α-olefin oligomerization reaction activity.

In the present invention, substituted or non-substituted α-olefins having 2 to 20 carbon atoms can be used as starting α-olefin. Examples of such α-olefins are ethylene, propylene, 1-butene, 1-hexene, 1-octene, 3-methyl-1-butene, 4-methyl-1-pentene and the like. Ethylene is particularly preferred as its trimer 1-hexene can be produced therefrom in a high yield with high selectivity.

As a reaction solvent, there can be used chain or alicyclic saturated hydrocarbons having 1 to 20 carbon atoms, such as butane, pentane, 3-methylpentane, hexane, heptane, 2-methylhexane, octane, cyclohexane, methylcyclohexane, 2,2,4-trimethylpentane, decalin, etc., and aromatic hydrocarbons such as benzene, toluene, xylene, ethylbenzene, mesitylene, tetralin, etc. These solvents may be used either singly or in admixture.

As a reaction solvent, it is possible to use the α-olefin supplied as reactant or other sources of α-olefin. In the present invention, α-olefins having 4–30 carbon atoms, preferably α-olefins which are liquid at ordinary temperature, are used as reaction solvent.

It is preferred to use $C_4$–$C_{10}$ chain or alicyclic saturated hydrocarbons as reaction solvent, because use of these solvents suppresses formation of the by-product polymers, and further when using an alicyclic hydrocarbon, a high catalytic activity can be obtained.

In the present invention, the amount of the chromium compound (a) allowed to exist is usually in a range from $1\times10^{-7}$ to 0.5 mol, preferably from $5\times10^{-7}$ to 0.2 mol, more preferably from $1\times10^{-6}$ to $5\times10^{-2}$ mol per liter of the solvent. The amount of the nitrogen-containing compound (b) is usually in a range from $1\times10^{-7}$ to 0.1 mol, preferably from $5\times10^{-7}$ to $5\times10^{-2}$ mol, more preferably from $1\times10^{-6}$ to $1\times10^{-2}$ mol per liter of the solvent. The amount of the alkylaluminum compound (c) is usually in a range from $1\times10^{-7}$ to $7\times10^{-2}$ mol, preferably from $5\times10^{-7}$ to $5\times10^{-2}$ mol, more preferably from $1\times10^{-6}$ to $1\times10^{-2}$ mol per liter of the solvent. The amount of the halogen-containing compound is usually in a range from $1\times10^{-7}$ to 0.1 mol, preferably from $5\times10^{-7}$ to $5\times10^{-2}$ mol, more preferably from $1\times10^{-6}$ to $1\times10^{-2}$ mol per liter of the solvent.

In the present invention, the molar ratio of chromium compound (a), at least one nitrogen-containing compound (b) selected from the group consisting of amines, amides and imides, alkylaluminum compound (c) and halogen-containing compound (d) in the reaction system ((a): (b): (c): (d)) is usually 1:0.1–100:0.1–500:0.1–100, preferably 1:0.1–10:1–100:0.1–20, more preferably 1:1–5:5–50:1–10. By combining these specific conditions, it is possible to produce the desired α-olefin oligomer, for example hexene, in a yield of not less than 90% by weight based on the overall production. Further, the 1-hexene content in the produced hexene can be elevated to not less than 99%.

Reaction temperature is usually in a range from 0° to 250° C., preferably from 0° to 150° C., more preferably from 20° to 100° C. Reaction pressure can be selected from a range from ordinary pressure to 250 kg/cm², preferably 3 to 100 kg/cm². Reaction time is usually in a range from one minute to 20 hours, preferably from 0.5 to 6 hours. It is advisable to let hydrogen exist in the reaction system since this leads to an enhancement of catalytic activity and trimer selectivity. The presence of hydrogen is also helpful for reducing the by-product polymers into a powdery form with small tackiness. The amount of hydrogen allowed to exist is usually in a range from 0.1 to 100 kg/cm², preferably from 0.1 to 80 kg/cm², in terms of partial pressure of hydrogen.

In the present invention, the catalyst components and the by-product polymer are recovered simultaneously from the oligomerization reaction solution. The recovery methods usable in the present invention include the following:

1) The α-olefin oligomer is distilled away from the oligomerization reaction solution, and the remaining by-product polymer and catalyst components are concentrated and recovered together.

2) The catalyst components and by-product polymer are separated together from the oligomerization reaction solution, and then the α-olefin oligomer is distilled away from the reaction solution.

In the conventional α-olefin oligomer production process, the by-product polymers and the catalyst components are separated by the separate operations. In this case, a solid/liquid separator for the by-product polymers is required separately from the one used for separation of the metal components, resulting in a complicated process and high equipment cost. Also, it becomes very difficult to separate the metal components which have been metallized due to the heat history applied during distillation separation of the components in the reaction solution. For instance, when it is tried to separate the high-boiling components and the metal components by utilizing a heating evaporator, it proves substantially unable to separate the metal components since they are deposited on the heating area of the evaporator. Further, the metal components deposited on the heating area tend to interfere with running of the evaporator.

On the other hand, according to a method of the present invention, for instance, in the above-mentioned method 1), since the by-product polymer is concentrated and recovered together with the catalyst components, the catalyst components can be very easily recovered owing to plasticity of the by-product polymer. Further, it is possible to dispense with the solid/liquid separator for the by-product polymer, thereby allowing a substantial simplification of the process.

In the above-mentioned method 1) of the present invention, the concentration and recovery of the by-product polymer and catalyst components can be accomplished simultaneously with simple distillation separation of the whole low-boiling components from the degassed reaction solution. It can also be accomplished simultaneously with final distillation separation in case where the component materials are distilled and separated successively from the degassed reaction solution. For instance, in case where the starting α-olefin is ethylene, 1-hexene is obtained as the α-olefin oligomer. In this case, ethylene is removed from the reaction product, and then 1-hexene and the solvent are distilled away from the reaction solution while the catalyst components are concentrated and recovered together with the by-product polyethylene. The concentrated solution containing the by-product polymer and catalyst components may be discarded in the form as it is.

In the present invention, at least part of the by-product polymer and at least part of the catalyst components are recovered simultaneously, but it is preferable to conduct such simultaneous recovery for all of the catalyst components, more preferably for all of both by-product polymer and catalyst components. In either case, the catalyst components concentrated and recovered together with the by-product polymer in the distillation separation operation are preferably further concentrated by a heating evaporator, thereby recovering the catalyst components.

It is possible to use known heating evaporators such as a thin-film evaporator having a scraper blade which turns along the heating area in the cylinder, or an evaporator incorporated with a plate fin type heater. In the latter evaporator, a high-viscosity fluid c an be heated instantaneously by the fins arranged at high density to allow efficient removal of the volatile substances contained in the fluid. A typical example of this type of evaporator is "Hiviscus Evaporator" (trade name, manufactured by Mitsui Zosen Co., Ltd.). According to the heating evaporator, the by-product polymer and catalyst components concentrated by the built-in plate fin-type heater flow down from the bottom of the evaporator due to plasticity of the by-product polymer, so that they can be easily recovered by cutting them in a properly cooled state.

An especially recommendable heating evaporator used in the present invention is a monotube evaporator provided with a heating pipe having a sufficient length and a recovery tank which is capable of retaining a vacuumized state. An example of this type of evaporators is "CRUX SYSTEM" (trade name, manufactured by Hosokawa Micron Co. Ltd.). In this monotube evaporator, the concentrated solution formed on heating and evaporation by the heating pipe is injected into the recovery tank at a high speed substantially equal to the acoustic velocity to efficiently remove the volatile substances contained in the concentrated solution. The by-product polymer and catalyst components concentrated in the recovery tank flow down from the bottom of the recovery tank due to plasticity of the by-product polymer, so that they can be easily recovered by cutting them in a properly cooled state.

In the above-mentioned method 2) of the present invention, the catalyst components and by-product polymer are precipitated and they can be separated simultaneously with a single solid/liquid separator, so that the process can be remarkably simplified and a stable operation is ensured without causing contamination of the distillation tower.

In the method 2) of the present invention, the reaction solution discharged from the reactor is fed into a degassing tank where the solution is degassed and the by-product polymer dissolved therein is precipitated. During this operation, the reaction solution needs to be maintained at a temperature less than 80° C. If the solution temperature is not less than 80° C., the by-product polymer nay be dissolved in the solution.

Then the catalyst components in the reaction solution are precipitated. Various precipitation methods are available, such as subjecting the reaction solution to an oxidation treatment with an oxidative gas or an oxidizing agent, or subjecting the reaction solution to a reducing treatment with a reducing agent.

In case of conducting an oxidation treatment with an oxidative gas, there can be used oxygen, ozone, chlorine dioxide ($ClO_2$), chlorine, nitrogen oxide ($N_2O$, $NO$, $N_2O_3$ and $N_2O_4$) and the like as oxidative gas, but oxygen or a mixed gas of oxygen and an inert gas is preferred, and air is most recommendable for the reasons of economy and safety. The oxidation treatment with an oxidative gas may be implemented by various methods such as (A) retaining the reaction solution in an oxidizing gas atmosphere, or (B) introducing an oxidizing gas into the reaction solution.

In the above-mentioned method (A), the reaction solution is retained in an oxidizing gas atmosphere with a concentration of 0.1 to 100 vol %, preferably 0.1 to 20 vol % at a temperature of 0° to 100° C., preferably 10° to 80° C. for a period of 0.02 to 50 hours, preferably 0.5 to 24 hours.

In the above-mentioned method (B), a 0.01 to 20 vol %, preferably 0.1 to 10 vol % oxidizing gas is introduced bubbling into the reaction solution at a temperature of 0° to 100° C., preferably 10° to 800° C., for a period of 0.01 to 50 hours, preferably 0.01 to 2 hours.

In either of these methods, it is important to select the conditions that minimize formation of the peroxides from the above-defined ranges. The oxidation treatment of the reaction solution may be carried out in the presence of an antioxidant so as not to allow formation of peroxides. Various types of antioxidant, such as quinones, aromatic amines, phenol derivatives, phosphonic acid esters, sulfur compounds, phosphorus compounds, sulfur-phosphorus compounds, dialkyl selenide, phenothiazine and the like may be used for the treatment. The oxidizing gas may be diluted with an inert gas such as nitrogen or argon gas.

In case of conducting an oxidation treatment with an oxidizing agent, various types of known oxidizing agents may be used, which include, for example, sulfur; peroxides such as hydrogen peroxide; various salts of heavy metal ions (silver (I), silver (II), lead (IV), etc.) with very low ionization tendency; various salts of metal ions (iron (III), cobalt (III), chrome (VI), manganese (III), cerium (IV), etc.) which can have various valences, and oxides thereof. Of these substances, silver (I) salt, cobalt (III) salt, chrome (VI) salt, manganese (III) salt, cerium (IV) salt and sulfur are preferred because of ease of treatment and safety.

The oxidation treatment with an oxidizing agent is preferably carried out in an inert gas (such as nitrogen, etc.) atmosphere at 0° to 100° C., preferably 10° to 80° C. for about 0.1 to 48 hours, preferably about 0.25 to 24 hours. It is considered that by this oxidation treatment, the chromium compound in the reaction solution is oxidized to cause a change of form of the catalyst and a drop of solubility, thereby inducing precipitation of the catalyst components.

In case of conducting a reduction treatment with a reducing agent, various types of known reducing agents can be used, which include zinc, sodium, potassium, magnesium, etc. Zinc and magnesium are preferred for the reasons of economy, ease of treatment and safety.

The reduction treatment with a reducing agent is preferably carried out in an inert gas (such as nitrogen, etc.) atmosphere at 0° to 100° C., preferably 10° to 80° C. for about 0.1 to 48 hours, preferably about 0.25 to 24 hours. As the reaction solution is contacted with the reducing agent, the chromium compound is precipitated and can be removed as the obtained precipitate.

Since the catalyst components are precipitated by the above oxidation or reduction treatment, the catalyst components can be separated and removed simultaneously with the by-product polymer in the reaction solution. Separation of the precipitated catalyst components and by-product polymer can be accomplished by using a known solid/liquid separator, without causing dissolution of the by-product polymer. A filter or a centrifugal separator is preferably used as solid/liquid separator.

In a preferred embodiment of the above-mentioned method 1) in the present invention, in order to effectively conduct the simultaneous recovery process of the by-product polymer and the catalyst components by taking advantage of plasticity of the by-product polymer, both by-product polymer and catalyst components are maintained in a dispersed state in the reaction solution in the process line from the outlet of the oligomerization reactor to the inlet of the distillation tower, thereby preventing loss of the said both substances till reaching the said simultaneous recovery process. The "dispersed state" referred herein includes not only a usual suspension state but also a solved state. In this embodiment, it is possible to avoid various troubles resulting from deposition or precipitation of the said substances in the process line (including accessory equipment such as piping and distillation tower).

Various methods, especially those mentioned below, can be used for maintaining the by-product polymer and catalyst components in a dispersed state in the reaction solution.

(I) Method of maintaining the temperature of the reaction solution in the process line from the outlet of the oligomerization reactor to the inlet of the distillation tower at a level not causing precipitation of the by-product polymer.

(II) Method of introducing hydrogen into the gas phase in the oligomerization reactor.

(III) Method of adding a compound soluble in the reaction solvent and having a bonding ability to chromium into the reaction solution in the process line from the outlet of the oligomerization reactor to the inlet of the distillation tower.

Addition of an antistatic agent to the reaction solution, which has already been proposed in the art of α-olefin oligomerization, is also a recommendable method.

The above-mentioned method (I) is one for maintaining the dispersed state of principally the by-product polymer in the reaction solution. In this method, the reaction solution is maintained at a temperature which does not cause precipitation of the by-product polymer, usually not less than 80° C. or above, preferably 80° to 200° C., more preferably 100° to 150° C. Even when a temperature of 100° to 150° C., most preferred for the purpose of the method, is adopted, the reaction performance is not reduced since such temperature is applied to the reaction solution discharged from the oligomerization reactor.

The above-mentioned method (II) is one for maintaining the dispersed state of the by-product polymer in the reaction solution by turning the by-product polymer into a powder form having small tackiness. This method also contributes to the enhancement of catalytic activity and trimer selectivity. The amount of hydrogen allowed to exist in the oligomerization reactor in this method is usually in the range 0.1 to 100 kg/cm$^2$, preferably 0.1 to 80 kg/cm$^2$ in terms of partial pressure of hydrogen, and in the range 0.1 to 30 vol %, preferably 0.1 to 15 vol % in terms of hydrogen concentration in the gas phase in the reactor.

The above-mentioned method (III) is one for maintaining the dispersed state of principally the catalyst components in the reaction solution. This method also has the effect of maintaining dispersion of the by-product polymer by converting it into powdery form having a small tackiness. As the compound soluble in the reaction solvent and having a bonding ability to chromium (this compound being hereinafter referred to as metal solubilizing agent), there is usually used a low-molecular weight compound having a —X—H functional group (wherein X is hetero atom and H is hydrogen atom) or a low-molecular weight compound having an active methylene group. Examples of the former compound include alcohols, phenols, carboxylic acids, primary or secondary amines, and ammonia. An example of the latter compound is acetylacetone.

The said alcohols include methanol, ethanol, propanol, butanol, pentanol, hexanol, heptanol, octanol, nonanol, decanol, benzyl alcohol, ethylene glycol, trimethylene glycol, and propanediol. The said phenols include phenol, cresol, and hydroquinone. Examples of the said carboxylic acids include acetic acid, propionic acid, butyric acid, valeric acid, hexanoic acid, heptanoic acid, octanoic acid, nonanoic acid, decanoic acid, benzoic acid, phenylacetic acid, phthalic acid, malonic acid, succinic acid, glutaric acid, adipic acid, acrylic acid, maleic acid, fumaric acid, and salicylic acid. The amines mentioned above as a catalyst constituent may be cited as typical examples of the said primary or secondary amines.

The percentage of the metal solubilizing agent used may be selected from a wide range from a trace amount to a solvent equivalent, but it is preferably in a range from 0.001 to 50% by weight, more preferably 0.01 to 10% by weight in terms of concentration in the solvent. The timing of addition of the said metal solubilizing agent may be at any stage before distillation separation of each component in the reaction solution. In case where a plural number of distillation separation steps are involved, the said metal solubilizing agent may be added immediately before the final distillation step where metallization of the metal substances is most likely to take place, but it is preferably added immediately after the reaction process.

In this embodiment of the present invention, the reaction solution discharged from the oligomerization reactor is fed into a degassing tower to recover the unreacted portion of α-olefin. Thus, in this embodiment, the degassing of the reaction solution is conducted prior to other unit operations. In the conventional industrialized α-olefin oligomerization process, unlike in the said embodiment of the present invention, separation of the by-product polymer has been conducted separately from the catalyst components by using a solid/liquid separating apparatus. In such conventional process, separation of the by-product polymer is carried out with the pressure in the reaction system maintained substantially unchanged. This is for the reason that in the production of 1-hexene by the said conventional process, the yield of 1-hexene is not sufficiently high and the process is attended by formation of a large amount (not less than about 15 wt %) of low-boiling point by-product substance (1-butene), so that if the pressure in the reaction system is reduced close to ordinary pressure after the reaction, the cooling load necessary for distillation separation of 1-butene (boiling point: −6.47° C.) from the unreacted ethylene is increased.

Therefore, in the said conventional process, the separation of the by-product polymer is conducted after the reaction without lowering the pressure, and then 1-butene is separated by distillation, with the pressure being reduced gradually in the ensuing unit operations. However, this method of separating the by-product polymer under pressure has many disadvantages such as necessity of a specific solid/liquid separator, poor operation efficiency, and sometimes clogging of the solid/liquid separator with the by-product polymer.

In contrast, in an oligomerization of α-olefins by use of a specific chromium-based catalyst system of the present invention, the formation of the α-olefin oligomers other than 1-hexene, especially 1-butene, is reduced and 1-hexene can be obtained in a high yield, so that there is no need of recovering 1-butene, and even in case it is recovered by ordinary pressure distillation, the cooling load necessary for distillation separation is markedly lessened. Consequently, it is possible in the process of the present invention to carry out degassing of the reaction solution before other unit operations. This leads to the advantages that the complicated steps in the said conventional process and its disadvantages mentioned above can be eliminated, and the succeeding unit operations can be conducted at a pressure close to ordinary pressure at which the operation efficiency is high.

In this embodiment of the present invention, the degassing of the reaction solution is carried out by lowering the pressure usually to not more than 15 kg/cm²G, but in view of the regulations on handling of pressure vessels, it is preferable to reduce the pressure to not more than 1.9 kg/cm²G. Even more preferably, the pressure is reduced to not more than 0.2 kg/cm²G as it is possible to conduct the substantially same operations as it is under ordinary pressure.

Then the reaction solution from the degassing tower is supplied into a distillation tower and the produced α-olefin oligomer is recovered as distillate while the by-product polymer and catalyst components are concentrated and recovered as bottoms. In the present invention, concentration and separation of the by-product polymer and catalyst components from the reaction solution can be conducted simultaneously with single distillation separation of the whole low-boiling substances from the degassed reaction solution, or performed simultaneously with final run of distillation in case the respective substances are distilled and separated successively from the degassed reaction solution.

For instance, in case where the α-olefin is ethylene, 1-hexene is obtained as α-olefin oligomer, and in this case, the reaction solution is first degassed and then 1-hexene and solvent are distilled and separated from the reaction solution while the catalyst components are concentrated and separated together with the by-product polymer. Thus obtained concentrated solution containing the by-product polymer and catalyst components may be discarded in the form as it is.

As described above, according to the process using the chromium-based catalyst system of the present invention, 1-hexene can be obtained in a high yield while formation of by-product 1-butene is minimized, so that by treating the reaction solution from the degassing tower by a single distillation tower, it can be separated into 1-hexene, reaction solvent and high boiling point products containing by-product polymer and catalyst components. Thus, a process with maximized simplicity and high economical efficiency is realized.

The recovered α-olefin oligomer is purified as desired. Distillation is usually used for purification, whereby the objective substance can be recovered with high purity. According to the process of the present invention, it is possible to produce, in particular, high-purity 1-hexene from ethylene in an industrially advantageous way. From 1-hexene obtained according to the process of the present invention, there can be produced a useful resin L-LDPE by a polymerization reaction using a known polymerization catalyst.

The process according to the present invention is an industrially advantageous process for the preparation of α-olefin oligomers by use of a chromium-based catalyst, which process is simple and capable of efficiently separating the by-product polymer together with the catalyst components.

EXAMPLES

The present invention is explained in more detail in the following examples and comparative examples, but it should be noted that the scope of the present invention is not limited to these examples.

Example 1

Continuous oligomerization reaction of ethylene was carried out using a production system comprising a continuous stirring tank reactor, a degassing tank, an ethylene distillation tower, a hexene distillation tower, a heptane distillation tower and an evaporator, with a compressor for circulating degassed ethylene to the reactor being provided between the said reactor and degassing tank. A 20-liter autoclave having two feed pipes was used as continuous stirring tank reactor, and "Hiviscuss Evaporator" (trade name, manufactured by Mitsui Zosen Co., Ltd.) was used as evaporator. The ethylene distillation tower had 15 plates, while the hexane distillation tower and the heptane distillation towers each had 20 plates.

An n-heptane solution of chromium (III) 2-ethylhexanoate and an n-heptane solution of 1,1,2,2-tetrachloroethane were continuously supplied with ethylene from one of the feed pipes of the reactor, while an n-heptane solution of 2,5-dimethylpyrrole and an n-heptane solution of triethylaluminum were supplied continuously from the other feed pipe.

The reaction solution discharged continuously from the reactor was supplied into the degassing tank. The degassed reaction solution was treated in the ethylene distillation tower, the hexene distillation and the heptane distillation tower successively. The bottoms of the heptane distillation tower was fed into the evaporator and concentrated. In the evaporator, the evaporated high boiling point products were condensed and recovered, while the concentrated catalyst components and by-product polymer were cooled and recovered as solid. Meanwhile, ethylene degassed in the degassing tank was pressurized by the compressor and circulated back to the reactor. n-Heptane separated in the heptane distillation tower was also circulated back to the reactor through a circulation pipe.

The operating conditions of the respective process units are shown in Table 1, and the mass balance in the process is shown in Table 2. In Table 2, $Cr(2EHA)_3$ denotes chromium (III)-2-ethylhexanoate.

TABLE 1

| Reactor | 80° C. × 35 kg/cm$^2$G |
|---|---|
| Degassing tank | 40° C. × 35 kg/cm$^2$G |
| Ethylene distillation tower | |
| Top pressure | 5 kg/cm$^2$G |
| Reflux ratio (R/D) | 0.5 |
| Hexene distillation tower | |
| Top pressure | 760 mmHg |
| Reflux ratio (R/D) | 3.0 |
| Heptane distillation tower | |
| Top pressure: | 760 mmHg |
| Reflux ratio (R/D) | 3.0 |
| Evaporator: | |
| Heating area | 0.125 m$^2$ |
| Heater temperature | 230° C. |
| Flash drum pressure | 100 mmHg |

TABLE 2

| | Reactor 26.1 kg/hr | De-gassing tank 22.6 kg/hr | Deheptanated solution 1.31 kg/hr | High boiling point products 1.30 kg/hr | Solids 2.8 g/hr |
|---|---|---|---|---|---|
| Cr salt (ppm)*$^1$ | 20.0 | 23.1 | 120 | — | 5.66 wt % |
| 2,5-Dimethylpyrrole (ppm) | 11.9 | 13.7 | 71.7 | 71.2 | — |
| Aluminum salt (ppm)*$^2$ | 71.1 | 82.3 | 427 | — | 20.1 wt % |
| Tetrachloroethane (ppm) | 34.9 | 40.3 | 209 | 209 | — |
| Heptane (wt %) | 30.9 | 35.8 | — | — | — |
| Ethylene (wt %) | 13.6 | — | — | — | — |
| 1-Hexene (wt %) | 50.5 | 58.4 | — | — | — |

TABLE 2-continued

| | Reactor 26.1 kg/hr | De-gassing tank 22.6 kg/hr | Deheptanated solution 1.31 kg/hr | High boiling point products 1.30 kg/hr | Solids 2.8 g/hr |
|---|---|---|---|---|---|
| High boiling point products (wt %) | 4.99 | 5.77 | 99.8 | 99.9 | — |
| Polyethylene (ppm) | 105 | 109 | 1574 | — | 74.2 wt % |

(Note):
*$^1$calculated as $Cr(2EHA)_3$
*$^2$calculated as triethylaluminum

In the evaporator operation in the above process, since the metal-containing catalyst components formed a concentrated mixture with by-product polyethylene, the concentrated mixture dropped gravitationally from the heating area due to polyethylene plasticity, and then were cooled and solidified.

Example 2

Continuous oligomerization of ethylene was carried out under the same conditions as in Example 1 except that chloroform was used in place of 1,1,2,2-tetrachloroethane. The mass balance in the process same as in Example 1 is shown in Table 3. The operations in the process could be conducted continuously with high stability as in Example 1.

TABLE 3

| | Reactor 35.0 kg/hr | De-gassing tank 30.3 kg/hr | Deheptanated solution 1.45 kg/hr | High boiling point products 1.42 kg/hr | Solids 28.7 g/hr |
|---|---|---|---|---|---|
| Cr salt (ppm)*$^1$ | 22.0 | 25.4 | 159 | — | 0.80 wt % |
| 2,5-Dimethylpyrrole (ppm) | 13.0 | 15.1 | 94.2 | 96.1 | — |
| Aluminum salt (ppm)*$^2$ | 78.2 | 90.5 | 565 | — | 2.86 wt % |
| Tetrachloroethane (ppm) | 38.3 | 44.3 | 277 | 283 | — |
| Heptane (wt %) | 41.3 | 47.8 | — | — | — |
| Ethylene (wt %) | 13.6 | — | — | — | — |
| 1-Hexene (wt %) | 41.0 | 47.4 | — | — | — |
| High boiling point products (wt %) | 4.07 | 4.71 | 98.0 | 99.9 | — |
| Polyethylene (ppm) | 1054 | 1097 | 1.90 wt % | — | 96.3 wt % |

(Note):
*$^1$calculated as $Cr(2EHA)_3$
*$^2$calculated as triethylaluminum

Example 3

Continuous oligomerization of ethylene was carried out under the same conditions as in Example 2 except that a monotube evaporator "CRUX SYSTEM" (trade name, manufactured by Hosokawa Micron Co., Ltd.) provided with an 8-m long heating pipe and an evacuatable recovery tank was used as evaporator. The evaporator operation was conducted at a heating pipe temperature of 200° C., a recovery tank temperature of 150° C. and a recovery tank pressure of 200 Torr. The mass balance in the process same as in Example 1 is shown in Table 4. The process could be operated continuously with stability as in Examples 1 and 2.

TABLE 4

|  | Reactor 36.1 kg/hr | De-gassing tank 31.2 kg/hr | Dehepta-nated solution 1.53 kg/hr | High boiling point products 1.45 kg/hr | Solids 82.5 g/hr |
|---|---|---|---|---|---|
| Cr salt (ppm)*[1] | 26.0 | 30.1 | 184 | — | 0.341 wt % |
| 2,5-Dimethylpyrrole (ppm) | 15.4 | 17.8 | 109 | 116 | — |
| Aluminum salt (ppm)*[2] | 92.5 | 107 | 656 | — | 1.21 wt % |
| Tetrachloroethane (ppm) | 45.3 | 52.5 | 321 | 340 | — |
| Heptane (wt %) | 41.1 | 47.6 | — | — | — |
| Ethylene (wt %) | 13.6 | — | — | — | — |
| 1-Hexene (wt %) | 41.0 | 47.4 | — | — | — |
| High boiling point products (wt %) | 4.07 | 4.63 | 94.6 | 99.9 | — |
| Polyethylene (ppm) | 3000 | 3125 | 5.32 wt % | — | 98.4 wt % |

(Note):
*[1]calculated as Cr(2EHA)₃
*[2]calculated as triethylaluminum

Comparative Example 1

1-Hexene was produced continuously according to the same procedure as in Example 1 except that a filter was set between the degassing tank and the ethylene distillation tower, and the degassed reaction solution was filtered to separate the by-product polyethylene. In the evaporator operation, the metal-containing catalyst components were resinified and deposited on the heating area, thereby making it unable to carry on the operation.

Example 4

The same procedure as in Example 1 was carried out except that a 2-liter autoclave having two feed pipes was used as reactor, and that an octanic acid (2-ethylhexanoic acid) was continuously supplied into the degassing tank as metal solubilizing agent. The operations could be conducted continuously with stability in the process. A part of the degassed reaction solution was sampled out and filtered to determine the shape of the by-product polyethylene. It was powdery.

The compositions of the solutions discharged from the reactor and the degassing tank respectively are shown in Table 5. The concentration of octanoic acid in the degassing tank shown in Table 5 is 0.022 wt % when converted to concentration in the reaction solvent.

TABLE 5

|  | Reactor 2,611 g/hr | Degassing tank 2,256 g/hr |
|---|---|---|
| Cr salt (wt %) | 0.002*[1] | 0.0028*[1] |
| 2,5-Dimethylpyrrole (wt %) | 0.001 | 0.0017 |
| Aluminum salt (wt %) | 0.009*[2] | 0.0010*[2] |
| Tetrachloroethane (wt %) | 0.004 | 0.0050 |
| Heptane (wt %) | 30.9 | 35.90 |
| Ethylene (wt %) | 13.6 | — |
| 1-Hexene (wt %) | 50.4 | 58.30 |
| High boiling point products (wt %) | 4.99 | 5.760 |

TABLE 5-continued

|  | Reactor 2,611 g/hr | Degassing tank 2,256 g/hr |
|---|---|---|
| Polyethylene (wt %) | 0.010 | 0.012 |
| Octanoic acid (wt %) | — | 0.008 |

(Note):
*[1]calculated as Cr(2EHA)₃
*[2]calculated as triethylaluminum

The bottoms of the heptane distillation tower was sampled out and analyzed to determine the precipitated metal substances. There was detected substantially no precipitated metal substance. The analysis for determining the precipitated metal substances was conducted in the following way. The sample was filtered by a filter paper (5A), the filter paper surface was washed with an n-heptane solution and then with a 10 wt % aqueous nitric acid solution, and the concentrations of the metal substances in the aqueous nitric acid solution were measured by high-frequency plasma emission spectroscopy.

Examples 5-8

1-Hexene was produced continuously according to the same procedure as in Example 1 except for using 1-hexanol (Example 5), hexylamine (Example 6), ammonia (Example 7) and acetylacetone (Example 8) as the metal solubilizing agent to be added to the degassing tank. In any of these examples, the metal solubilizing agent was added in such an amount that the concentration of the agent in the reaction solvent in the degassing tank would become 0.022% by weight. The bottoms of the heptane distillation tower was sampled out and analyzed for the precipitated metal substances in the same manner as in Example 4. There is existed substantially no precipitated metal substance in each example.

Example 9

Continuous production of 1-hexene was carried out according to the same procedure as in Example 4 except that no 2-ethylhexanoic acid was supplied to the degassing tank. The bottoms of the heptane distillation tower was sampled out and analyzed for the precipitated metal substances in the same way as in Example 4. As a result, chromium was detected in an amount equivalent to 96.3% by weight based on the amount supplied to the reactor. The precipitated chromium was maintained in a dispersed state in the piping. The catalyst components and the by-product polymer were concentrated simultaneously in the evaporator and then cooled and solidified. A part of the degassed reaction solution was sampled out and filtered to determine the shape of the by-product polyethylene. It was film-like and adhesive.

Example 10

Continuous oligomerization reaction of ethylene was carried out using a production a process system comprising a continuous stirring tank reactor, a degassing tank, a 30-plate distillation tower having two side stream outlets, and an evaporator, with a compressor for circulating the degassed ethylene to the reactor being provided between the said reactor and degassing tank. A 20-liter autoclave having two feed pipes was used as continuous stirring tank reactor, and a monotube evaporator "CRUX SYSTEM" (trade name, manufactured by Hosokawa Micron Co., Ltd.) having an 8-m long heating pipe and an evacuatable recovery tank was used as evaporator.

An n-heptane solution of chromium (III)-2-ethylhexanoate(a) and an n-heptane solution of 1,1,2,2- tetrachloroethane (d) were continuously supplied along with ethylene from one of the feed pipes of the reactor, while an n-heptane solution of 2,5-dimethylpyrrole (b) and an n-heptane solution of triethylaluminum (c) were supplied continuously from the other feed pipe. The molar ratio of (a):(b):(c):(d) was 1:3:15:2.

The reaction solution discharged continuously from the reactor was heated to 100° C. by the heater provided between the reactor and the degassing tank, and supplied into the degassing tank. The degassed reaction solution was fed into the distillation tower and the bottoms thereof was supplied into the evaporator and concentrated. The solvent n-heptane was recovered by taking it out from the side stream outlet in the eighth plate from bottom of the distillation tower while the product hexene was recovered by taking it out from the side stream outlet in the 26th plate. From the tower top, the substances having lower boiling points than hexene were distilled out and recovered.

The high boiling point products evaporated in the evaporation were recovered by condensing the substances, and the catalyst components concentrated together with the by-product polyethylene were recovered from the bottom of the recovery tank as solid. On the other hand, degassed ethylene was pressurized by the compressor and circulated back to the reactor, while n-heptane recovered from the distillation tower was also circulated back to the reactor via the circulation pipe. The operating conditions of the said units in the process are shown in Table 6, and the mass balance in the said process is shown in Table 7. In Table 7, $Cr(2EHA)_3$ denotes chromium (III) 2-ethylhexanoate.

TABLE 6

| Reactor | 80° C. × 35 kg/cm²G |
|---|---|
| Degassing tank | 100° C. × 5 kg/cm²G |
| Distillation tower | |
| Top pressure | 3 kg/cm²G |
| Reflux ratio (R/D) | 18 |
| Bottom temperature | 162° C. |
| Heating pipe temperature | 200° C. |
| Recovery tank temperature | 150° C. |
| Recovery tank pressure | 200 Torr |

TABLE 7

| | Reactor 36.1 kg/hr | De-gassing tank 31.2 kg/hr | Bottom of the distillation tower 1.57 kg/hr | High boiling point products 1.47 kg/hr | Solids 98.8 g/hr |
|---|---|---|---|---|---|
| Cr salt (ppm)*¹ | 26.0 | 30.1 | 180 | — | 0.285 wt % |
| 2,5-Dimethylpyrrole (ppm) | 15.4 | 17.8 | 106 | 113 | — |
| Aluminum salt (ppm)*² | 92.5 | 107 | 638 | — | 1.01 wt % |
| Tetrachloroethane (ppm) | 45.3 | 52.4 | 313 | 333.8 | — |
| Heptane (wt %) | 41.1 | 47.5 | — | — | — |
| Ethylene (wt %) | 13.6 | — | — | — | — |
| 1-Hexene (wt %) | 41.0 | 47.4 | — | — | — |
| High boiling point products (wt %) | 4.07 | 4.71 | 93.7 | 100.0 | — |
| Polyethylene (ppm) | 3000 | 3469 | 6.21 wt % | — | 98.7 wt % |

(Note):
*¹calculated as $Cr(2EHA)_3$
*²calculated as triethylaluminum

The evaporator operation in the above process was conducted smoothly. Since the metal-containing catalyst components are recovered as a concentrated mixture with by-product polyethylene, they dropped gravitationally from the bottom of the recovery tank owing to plasticity of the by-product polymer and separated.

Example 11

Continuous oligomerization of ethylene was carried out according to the same procedure as in Example 10 except that hydrogen was added to provide a hydrogen concentration of 2.0 vol % in the gas phase in the reactor, and that the reaction solution supplied to the degassing tank was not heated. Polyethylene in the reaction solution discharged from the reactor was powdery. The mass balance of this example is shown in Table 8. The evaporator operation was conducted smoothly as in Example 10.

TABLE 8

| | Reactor 36.1 kg/hr | De-gassing tank 31.2 kg/hr | Deheptanated solution 1.58 kg/hr | High boiling point products 1.47 kg/hr | Solids 109.6 g/hr |
|---|---|---|---|---|---|
| Cr salt (ppm)*¹ | 26.0 | 30.1 | 178 | — | 0.257 wt % |
| 2,5-Dimethylpyrrole (ppm) | 15.4 | 17.8 | 106 | 113.5 | — |
| Aluminum salt (ppm)*² | 92.5 | 107 | 634 | — | 0.91 wt % |
| Tetrachloroethane (ppm) | 45.3 | 52.4 | 311 | 333.8 | — |
| Heptane (wt %) | 41.1 | 47.5 | — | — | — |
| Ethylene (wt %) | 13.6 | — | — | — | — |
| 1-Hexene (wt %) | 41.0 | 47.4 | — | — | — |
| High boiling point products (wt %) | 4.07 | 4.71 | 93.0 | 100.0 | — |
| Polyethylene (ppm) | 3000 | 3469 | 6.86 wt % | — | 98.8 wt % |

(Note):
*¹calculated as $Cr(2EHA)_3$
*²calculated as triethylaluminum

Example 12

Continuous oligomerization of ethylene was carried out according to the same procedure as in Example 10 except that an octanoic acid (2-ethylhexanoic acid) was added continuously as metal solubilizing agent to the degassing tank, and that the reaction solution supplied to the degassing tank was not heated. The metal solubilizing agent was added in such an amount that its concentration in the reaction solvent in the degassing tank would become 0.022 wt %.

The bottoms of the distillation tower was sampled out and analyzed for the precipitated metal substances, but there was detected substantially no precipitated metal substance. Analysis for the precipitated metal substances was made in the following way. The sample was filtered with a filter paper (5A), the filter paper surface was washed with an n-heptane solution and then with a 10 wt % aqueous nitric acid solution, and the concentrations of the metal substances in the nitric acid solution were measured by high-frequency plasma emission spectroscopy. Polyethylene in the reaction solution discharged from the degassing tank was powdery. The mass balance of this example is shown in Table 9. The evaporator operation was conducted smoothly as in Example 10.

TABLE 9

| | Reactor 36.1 kg/hr | De-gassing tank 31.2 kg/hr | Bottom of the distillation tower 1.57 kg/hr | High boiling point products 1.47 kg/hr | Solids 101.8 g/hr |
|---|---|---|---|---|---|
| Cr salt (ppm)*1 | 26.0 | 30.1 | 597 | — | 0.922 wt % |
| 2,5-Dimethylpyrrole (ppm) | 15.4 | 17.8 | 354 | 378.0 | — |
| Aluminum salt (ppm)*2 | 92.5 | 107 | 2122 | — | 3.28 wt % |
| Tetrachloroethane (ppm) | 45.3 | 52.4 | 1040 | 1111.7 | — |
| Heptane (wt %) | 41.1 | 47.5 | — | — | — |
| Ethylene (wt %) | 13.6 | — | — | — | — |
| 1-Hexene (wt %) | 41.0 | 47.4 | — | — | — |
| High boiling point products (wt %) | 4.07 | 4.71 | 93.4 | 99.9 | — |
| Polyethylene (ppm) | 3000 | 3469 | 6.20 wt % | — | 95.8 wt % |

(Note):
*1 calculated as Cr(2EHA)$_3$
*2 calculated as triethylaluminum

Examples 13–16

Continuous oligomerization of ethylene was carried out according to the same procedure as in Example 12 except that 1-hexanol (Example 13), hexylamine (Example 14), ammonia (Example 15) and acetylacetone (Example 16) were used as metal solubilizing agent added to the degassing tank. The evaporator operation was smooth as in Example 12. The bottoms of the distillation tower was sampled out and analyzed for the precipitated metal substances in the same way as in Example 12, but there was found substantially no precipitated metal substance in each example.

Comparative Example 2

Continuous oligomerization of ethylene was carried out according to the same procedure as in Example 10 except that a filter was installed between the degassing tank and the distillation tower, and that the degassed reaction solution was filtered to separate the by-product polyethylene. The evaporator was incapable of continuous operation as the metal-containing catalyst substances were resinified and deposited on the heating area.

Example 17

Continuous oligomerization reaction of ethylene was carried out using a production system comprising a continuous stirring tank reactor, a degassing tank, an aeration tank, a decanter, an ethylene distillation tower, a hexene distillation tower and a heptane distillation, and also having a compressor disposed between the reactor and the degassing tank for circulating degassed ethylene back to the reactor. A 2-liter autoclave having two feed pipes was used as reactor. "Sharples Superdecanter" (trade name, manufactured by Tome Kogyo Co., Ltd.) was used as decanter. The ethylene distillation tower had 15 plates while the hexene distillation tower and the heptane distillation tower each had 20 plates.

An n-heptane solution of chromium (III) 2-ethylhexanoate and an n-heptane solution of 1,1,2,2-tetrachloroethane were supplied continuously together with ethylene from one of the feed pipes of the reactor, while an n-heptane solution of 2,5-dimethylpyrrole and an n-heptane solution of triethylaluminum were supplied continuously from the other feed pipe.

The reaction solution discharged continuously from the reactor was supplied into the degassing tank. The temperature of the degassed reaction solution was 60° C. This reaction solution was fed into the aeration tank where the catalyst components in the solution were oxidized and precipitated by bubbling air through the solution. The precipitated catalyst components and by-product polymer were removed by the decanter. The supernatant solution was supplied into and treated in the ethylene distillation tower, the hexene distillation tower and the heptane distillation tower successively. Meanwhile, ethylene degassed in the degassing tank was pressurized by the compressor and circulated back to the reactor, and n-heptane separated in the heptane distillation tower was also circulated back to the reactor via the circulation pipe.

The operating conditions of the respective units in the said process are shown in Table 10, and the mass balance of the said process is shown in Table 11.

TABLE 10

| Reactor | 80° C. × 35 kg/cm$^2$G |
|---|---|
| Degassing tank | 60° C. × 5 kg/cm$^2$G |
| Aeration tank | 60° C. × 3 kg/cm$^2$G |
| Air Feed: | 100 l/hr |
| Ethylene distillation tower | |
| Top pressure | 5 kg/cm$^2$G |
| Reflux ratio (R/D) | 0.5 |
| Hexene distillation tower | |
| Top pressure | 760 mmHg |
| Reflux ratio (R/D) | 3.0 |
| Heptane distillation tower | |
| Top pressure: | 760 mmHg |
| Reflux ratio (R/D) | 3.0 |

TABLE 11

| | Reactor 2,611 g/hr | Degassing tank 2,262 g/hr | Decanter solution 2,262 g/hr |
|---|---|---|---|
| Cr salt (wt %) | 0.002*1 | 0.0028*1 | — |
| 2,5-Dimethylpyrrole (wt %) | 0.001 | 0.0017 | 0.0017 |
| Aluminum salt (wt %) | 0.009*2 | 0.0010*2 | — |
| Tetrachloroethane (wt %) | 0.004 | 0.005 | — |
| Heptane (wt %) | 30.9 | 35.8 | 35.8 |
| Ethylene (wt %) | 13.6 | 0.27 | 0.27 |
| 1-Hexene (wt %) | 50.4 | 58.2 | 58.2 |
| High boiling point products (wt %) | 4.99 | 5.75 | 5.75 |
| Polyethylene (wt %) | 0.010 | 0.011 | — |

(Note):
*1 calculated as Cr(2EHA)$_3$
*2 calculated as triethylaluminum

By conducting the above process, the catalyst components and the by-product polymer were separated simultaneously with ease and stability, and it was possible to obtain hexene with a high content of 1-hexene.

What is claimed is:

1. A process for producing an α-olefin oligomer using a chromium-based catalyst system comprising at least (a) a chromium compound, (b) at least one nitrogen-containing compound selected from the group consisting of amines, amides and imides, and (c) an alkylaluminum compound, which process comprises carrying out an oligomerization reaction of an α-olefin in a solvent, and recovering the produced α-olefin oligomer, catalyst components and by-product polymer from the reaction solution, wherein the catalyst components and the by-product polymer are recovered at the same time.

2. The process according to claim 1, wherein the α-olefin oligomer is separated by distillation from the reaction solution produced by the oligomerization reaction, and the by-product polymer is concentrated and recovered together with the catalyst components.

3. The process according to claim 2, wherein the catalyst components concentrated and recovered with the by-product polymer in the distillation separation operation are further concentrated by a heating evaporator and recovered.

4. The process according to claim 3, wherein the heating evaporator is a monotube-type reactor provided with a heating pipe having a sufficient length and a recovery tank which can be evacuated.

5. The process according to claim 2, in which the oligomerization of the α-olefin is carried out in a solvent, then a compound soluble in the solvent and having a bonding ability to chromium is added to the reaction solution, and the respective substances are distilled and recovered from the resultant reaction solution.

6. The process according to claim 5, wherein the compound having a bonding ability is a compound having a functional group: —X—H (wherein X is a hetero atom and H is a hydrogen atom) or a compound having an active methylene group.

7. The process according to claim 6, wherein the compound having a bonding ability is selected from the group consisting of alcohols, phenols, carboxylic acids, primary or secondary amines, ammonia and acetylacetone.

8. The process according to claim 1, in which the catalyst components and the by-product polymer are separated simultaneously from the reaction solution produced from the oligomerization reaction, and then the α-olefin oligomer is separated by distillation from the resultant reaction solution.

9. The process according to claim 1, wherein the chromium-based catalyst comprises a combination of (a) a chromium compound, (b) at least one compounds selected from the group consisting of amines, amides and imides, (c) an alkylaluminum compound, and (d) a halogen-containing compound.

10. The process according to claim 1, wherein the nitrogen-containing compound (b) is a compound having a pyrrole ring structure.

11. The process according to claim 10, wherein the nitrogen-containing compound (b) is pyrrole or 2,5-dimethylpyrrole.

12. The process according to claim 9, wherein the halogen-containing compound (d) is a compound containing an element selected from the group consisting of IIIA, IIIB, IVA, IVB, VA, VB and VIB Groups of the periodic table.

13. The process according to claim 12, wherein the halogen-containing compound (d) is a compound containing an element selected from the group consisting of IVA and IVB Groups of the periodic table.

14. The process according to claim 13, wherein the halogen-containing compound (d) is a compound selected from the group consisting of carbon tetrachloride, chloroform, dichloroethane, titanium tetrachloride, germanium tetrachloride, hexachloroethane and tin tetrachloride.

15. The process according to claim 1, wherein the molar ratio of the catalyst components (a):(b):(c) is 1:0.1–10:1–100.

16. The process according to claim 9, wherein the molar ratio of the catalyst components (a):(b):(c):(d) is 1:0.1–10:1–100:0.1–20.

17. The process according to claim 9, wherein each of the compound (a) to (d) and the α-olefin is supplied to a reaction system in such a mode that the chromium compound (a) and the alkylaluminum compound (c) do not contact with each other before each of said compounds (a) to (d) and the α-olefin coexist in the reaction solvent and the oligomerization of the α-olefin takes place.

18. The process according to claim 2, wherein the α-olefin is ethylene and the α-olefin oligomer is composed principally of 1-hexene, and after the oligomerization reaction, a degassing treatment is carried out, and then 1-hexene and the solvent are distilled and separated from the reaction solution while the catalyst components are concentrated and recovered together with the by-product polymer.

19. The process according to claim 1, wherein the reaction solvent is a chain or alicyclic saturated hydrocarbon having 4–10 carbon atoms.

20. The process according to claim 1, wherein the oligomerization reaction is carried out in the presence of hydrogen.

21. A process for producing an α-olefin oligomer, which comprises carrying out an oligomerization of an α-olefin in an oligomerization reactor in the presence of a reaction solvent by using a chromium-based catalyst system comprising at least (a) a chromium compound, (b) at least one nitrogen-containing compound selected from the group consisting of amines, amides and imides, and (c) an alkylaluminum compound, supplying the resulting reaction solution to a degassing tower to recover the unreacted portion of the α-olefin, supplying the reaction solution from the degassing tower to a product distillation tower, and recovering the produced α-olefin oligomer as a distillate while concentrating the by-product polymer and the catalyst components and recovering the obtained concentrate as bottoms, wherein the by-product polymer and the catalyst components are maintained in a dispersed state in the reaction solution in the process line from the outlet of the oligomerization reactor to the inlet of the product distillation tower.

22. The process according to claim 21, wherein the reaction solution is separated into the α-olefin oligomer, reaction solvent, and high boiling point products including the by-product polymer and the catalyst components by a single distillation tower.

23. The process according to claim 21, wherein the temperature of the reaction solution in the process line from the outlet of the oligomerization reactor to the inlet of the product distillation tower is maintained at a level which does not cause precipitation of the by-product polymer.

24. The process according to claim 21, wherein hydrogen is allowed to exist in the gas phase in the oligomerization reactor.

25. The process according to claim 21, wherein a compound soluble in the reaction solvent and having a bonding ability to chromium is added to the reaction solution in the process line from the outlet of the oligomerization reactor to the inlet of the product distillation tower.

26. The process according to claim 21, wherein the bottoms containing the by-product polymer and the catalyst components recovered from the product distillation tower is supplied to a heating evaporator to recover high-boiling point products, and the by-product polymer and catalyst components are further concentrated and recovered.

27. The process according to claim 26, wherein the heating evaporator is a monotube-type evaporator provided with a heating pipe having a sufficient length and a recovery tank capable of maintaining a vacuum therein.

28. The process according to claim 21, wherein the α-olefin is ethylene, and the α-olefin oligomer is composed principally of 1-hexene.

29. The process according to claim 28, wherein the reaction product is separated into 1-hexene, reaction solvent and high boiling point products including the by-product polymer and catalyst components by a single distillation tower.

* * * * *